United States Patent
Georgeson et al.

(10) Patent No.: US 7,367,236 B2
(45) Date of Patent: May 6, 2008

(54) NON-DESTRUCTIVE INSPECTION SYSTEM AND ASSOCIATED METHOD

(75) Inventors: Gary E. Georgeson, Federal Way, WA (US); Kenneth H. Griess, Kent, WA (US)

(73) Assignee: The Boeing Company, Chicago, IL (US)

( * ) Notice: Subject to any disclaimer, the term of this patent is extended or adjusted under 35 U.S.C. 154(b) by 109 days.

(21) Appl. No.: 11/186,021

(22) Filed: Jul. 21, 2005

(65) Prior Publication Data
US 2007/0017297 A1 Jan. 25, 2007

(51) Int. Cl.
*G01N 29/04* (2006.01)
(52) U.S. Cl. .................. 73/801; 73/12.09; 73/802
(58) Field of Classification Search ............. 73/801, 73/802, 12.12, 12.09
See application file for complete search history.

(56) References Cited

U.S. PATENT DOCUMENTS

| | | | |
|---|---|---|---|
| 4,058,003 A | 11/1977 | Macovski | |
| 5,073,814 A | 12/1991 | Cole, Jr. et al. | |
| 5,091,893 A | 2/1992 | Smith et al. | |
| 5,165,270 A | 11/1992 | Sansalone et al. | |
| 5,614,670 A | 3/1997 | Nazarian et al. | |
| 5,680,863 A | 10/1997 | Hossack et al. | |
| 5,735,282 A | 4/1998 | Hossack | |
| 5,814,731 A | 9/1998 | Alexander et al. | |
| 5,869,189 A | 2/1999 | Hagood, IV et al. | |
| 5,983,701 A | 11/1999 | Hassani et al. | |
| 6,370,964 B1 * | 4/2002 | Chang et al. | 73/862.046 |
| 6,424,597 B1 | 7/2002 | Bolomey et al. | |
| 6,476,541 B1 | 11/2002 | Smith et al. | |
| 6,586,702 B2 | 7/2003 | Wiener-Avnear et al. | |
| 6,598,485 B1 | 7/2003 | Lin et al. | |
| 6,656,124 B2 | 12/2003 | Flesch et al. | |
| 6,798,717 B2 | 9/2004 | Wiener-Avnear et al. | |
| 6,799,126 B1 * | 9/2004 | Ratcliffe et al. | 702/56 |

(Continued)

FOREIGN PATENT DOCUMENTS

EP 1 484 608 A2 12/2004

(Continued)

OTHER PUBLICATIONS

*The Impact-Echo Technology;* Impact-Echo Instruments, LLC; 2 pages, available at http://www.impact-echo.com/pages/technology.html; downloaded Jul. 5, 2005.

(Continued)

*Primary Examiner*—Edward Lefkowitz
*Assistant Examiner*—Punam Patel
(74) *Attorney, Agent, or Firm*—Alston & Bird LLP

(57) ABSTRACT

An assembly, system, and method for identifying defects in a structure are provided. The assembly includes a structure of a metallic or composite material, and a flexible sheet of material positioned adjacent to the structure. The assembly also includes a plurality of non-destructive sensors secured to the flexible sheet, and a mechanism operable to impact the flexible sheet or proximate to the flexible sheet to generate stress waves within and along a surface of the structure. The system further provides a data acquisition system capable of communicating with the sensors such that the data acquisition system generates feedback indicative of at least a portion of the structure based on data from the stress waves acquired by the sensors.

27 Claims, 4 Drawing Sheets

U.S. PATENT DOCUMENTS

| 6,822,374 | B1 | 11/2004 | Smith et al. | |
|---|---|---|---|---|
| 2003/0094031 | A1* | 5/2003 | Huang et al. | 73/12.09 |
| 2004/0123665 | A1 | 7/2004 | Blodgett et al. | |
| 2005/0068041 | A1* | 3/2005 | Kress et al. | 324/527 |
| 2007/0100582 | A1* | 5/2007 | Griess et al. | 702/183 |

FOREIGN PATENT DOCUMENTS

| WO | WO 94/13411 | 6/1994 |
|---|---|---|

OTHER PUBLICATIONS

Mary J. Sansalone and William B. Streett; *The Impact-Echo Method; NDTnet*, Feb. 1998, vol. 3, No. 2; 9 pages available at http://www.ndt.net/article/0298/streett/streett.htm.

*Impact-Echo Testing; Whitlock, Dalrymple, Poston & Associates;* 1 page, available at http://www.wdpa.com/impactecho.html; downloaded Jan. 5, 2005.

*Electrical and Electronic Engineering, NDT, Nondestructive Testing, NDE, Nondestruti . . . ; HD Laboratories, Inc.*; 2 pages, available at http://www.hdlabs.com; downloaded Mar. 25, 2005.

N.J. Carino; *The Impact-Echo Method: An Overview; National Institute of Standards and Technology*; pp. 1-18 (2001).

Kress K-P et al.; "Smart Wide-Area Imaging Sensor System(SWISS)" Proceedings of the Spie, Spie, Bellingham, VA, US; vol. 4332, Mar. 5, 2001; pp. 490-496, XP008014768; ISSN: 0277-786X.

PCT Notification of Transmittal of the International Search Report and the Written Opinion of The International Searching Authority, or the Declaration, mailed Nov. 24, 2006 for PCT/US2006/026187 (Filed Jul. 5, 2006).

Lee et al., "New Tools for Structural Testing—Piezoelectric Impact Hammers and Acceleration Rate Sensors," *Proceedings from the 35th Aerospace Sciences Meeting and Exhibit*, Reno, NV, Jan. 6-9, 1997, pp. 1-8.

\* cited by examiner

NON-DESTRUCTIVE INSPECTION SYSTEM AND ASSOCIATED METHOD

BACKGROUND OF THE INVENTION

1) Field of the Invention

The present invention relates to non-destructive inspection and, more particularly, to non-destructive inspection of a structure for defects using an impact echo method.

2) Description of Related Art

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse-echo, or mechanical impedance sensors are typically used to provide indications of voids or porosity, such as in adhesive bond-lines of the structure. High resolution inspection of aircraft structure is commonly performed using ultrasonic testing (UT) to provide a plan view image of the part or structure under inspection. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors.

Non-destructive inspection may be performed manually by technicians who typically move an appropriate sensor over the structure. Manual scanning requires a trained technician to move the sensor over all portions of the structure needing inspection. Manual scanning typically involves the technician repeatedly moving a sensor side-to-side in one direction while simultaneously indexing the sensor in another direction. In addition, because sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have also been developed. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear-wave, and through-transmission sensors. The fixed frame may be attached to a surface of a structure to be inspected by vacuum suction cups, magnets, or like affixation methods. Smaller MAUS systems may be portable units manually moved over the surface of a structure by a technician.

Automated inspection systems have also been developed. For example, the Automated Ultrasonic Scanning System (AUSS®) system is a complex mechanical scanning system that may employ through-transmission ultrasonic inspection. An AUSS system can also perform pulse-echo inspections, and simultaneous dual frequency inspections. The AUSS system has robotically controlled probe arms that may be positioned, for example, for TTU inspection proximate the opposed surfaces of the structure undergoing inspection with one probe arm moving an ultrasonic transmitter along one surface of the structure, and the other probe arm correspondingly moving an ultrasonic receiver along the opposed surface of the structure. To maintain the ultrasonic transmitter and receiver in proper alignment and spacing with one another and with the structure undergoing inspection, a conventional automated inspection system may have a complex positioning system that provides motion control in numerous axes, such as the AUSS-X system which has motion control in ten axes. Automated inspection systems and like robotics, however, can be prohibitively expensive. Further, orienting and spacing sensors with respect to the structure, and with respect to one another for TTU inspection, may be especially difficult in conjunction with structures with non-planar shapes, such as the inspection of curved structures and hat stringers. Also, conventional automated scanning systems, such as the AUSS-X system, may require access to both sides of a structure which, at least in some circumstances, will be problematic, if not impossible, particularly for very large or small structures. Furthermore, scanning systems inspect limited areas up to a few meters square.

Other inspection techniques have been utilized to inspect non-composite and non-metallic structures. For example, a technique used to inspect concrete and masonry materials is the impact-echo method. The impact-echo method was developed in the 1980's where a small sphere was used to generate short duration mechanical impact. It was discovered that by varying the diameter of the sphere and the impact force of the sphere, stress waves could be generated through concrete structural elements to discover internal flaws and defects. The time-of-flight diffraction technique includes impacting the concrete to generate longitudinal (P), shear (S), and surface (R) waves. The location of a defect may be determined by monitoring the speed of the stress waves. In particular the P and S waves are reflected by internal defects or external boundaries. When the reflected waves, or echoes, return to the surface, they produce displacements that are measured by a receiving transducer. The impact-echo technique typically requires an impactor to generate stress waves, a receiving transducer unit, an A/D-converter, and a computer installed with waveform analysis software to process the collected signals. A further discussion of the impact-echo method is disclosed in "The Impact-Echo Method," by Mary J. Sansalone and William B. Street, NDTnet, The Online Journal of Nondestructive Testing & Ultrasonics, Vol. 3, No. 2 (February 1998), which is incorporated herein by reference.

Despite utilizing impact-echo techniques to conduct non-destructive inspection of concrete and masonry structures, improvements are desired to inspect for various defects within a structure. In particular, an inspection system that is versatile and capable of being used for non-destructive inspection beyond concrete and masonry structures, such as for composites and metallic structures, is desired. Because composites and metallic structures used, for example, in the airline industry are typically much thinner than concrete and masonry structures tested by the impact-echo method, the stress waves mainly travel along the surface of the structure. Therefore, the collection and analysis of the stress waves through the metallic or composite structure is unlike those of stress waves traveling through concrete or masonry structures.

It would therefore be advantageous to provide a non-destructive inspection system that is capable of employing the impact-echo method for materials other than concrete or masonry. In addition, it would be advantageous to provide an inspection system that is portable and capable of inspecting structures effectively and efficiently. Furthermore, it would be advantageous to provide a non-destructive inspection system that is economical to manufacture and use.

BRIEF SUMMARY OF THE INVENTION

Embodiments of the invention address the above needs and achieve other advantages by providing an inspection system that utilizes the impact-echo technique to inspect a structure for flaws. In particular, the system is capable of inspecting composite and metallic structures using the impact-echo method. The inspection system incorporates a flexible sheet of material having several sensors secured thereon. An impact mechanism is used to generate stress waves in and along the surface of the structure. The sensors communicate with a data acquisition system to generate images that identify flaws within the structure. Employing the impact-echo method allows the inspection system to inspect composite and metallic structures more rapidly and at a lower cost than conventional inspection techniques.

In one embodiment, an assembly for identifying defects in a structure is provided. The assembly includes a structure of a metallic or composite material, and a flexible sheet of material positioned adjacent to the structure. The assembly also includes a plurality of non-destructive sensors secured to the flexible sheet, and a mechanism operable to impact the flexible sheet or proximate to the flexible sheet to generate stress waves within and along a surface of the structure.

In aspects of the assembly, the flexible sheet of material includes a non-conductive material, such as a polymeric material. The flexible sheet of material is capable of being secured to the structure using a vacuum bag, vacuum frame, an adhesive backing, or an ultrasonic gel. The sensors are typically piezo-electric sensors. The sensors may be arranged about the periphery of the flexible sheet of material or in a grid about the flexible sheet of material. In addition, the mechanism may include a tapper, a tapper having a spring-loaded bar, one or more clickers, or a hammer.

Embodiments of the present invention also provide a system for identifying defects in a structure. The system includes a flexible sheet of material positioned adjacent to the structure, and a plurality of non-destructive sensors secured to the flexible sheet. The system also includes a mechanism operable to impact the flexible sheet or proximate to the flexible sheet at a plurality of locations to generate stress waves within and along a surface of the structure, as well as a data acquisition system capable of communicating with the sensors such that the data acquisition system generates feedback indicative of at least a portion of the structure based on data from the stress waves acquired by the sensors. The structure could be a metallic or composite material. The data acquisition system may include a processor for creating an image that includes information for detecting a defect in the structure.

The present invention also provides a method for identifying defects in a structure utilizing a plurality of non-destructive sensors secured to a flexible sheet of material. The method includes positioning the flexible sheet of material adjacent to a structure. The method also includes impacting the flexible sheet or proximate to the flexible sheet at a plurality of locations to generate stress waves within and along a surface of the structure. The method further includes detecting the stress waves with the sensors and deriving data from the stress waves that is indicative of at least a portion of the structure.

In various aspects of the method, the method includes securing the flexible sheet of material to the structure using a vacuum bag, vacuum frame, an adhesive backing, or an ultrasonic gel. The method may also include impacting the flexible sheet of material with a tapper, a tapper having a spring-loaded bar, one or more clickers, or a hammer. Additional aspects of the method include impacting the flexible sheet of material manually or automatically. The method could include impacting about the periphery of the flexible sheet of material or in predetermined or arbitrary patterns. The method could further include communicating the data acquired by the sensors to a data acquisition system and creating an image of at least a portion of the structure with the data acquisition system based on the data acquired by the sensors.

A further embodiment of the present invention provides a system for identifying defects in an aircraft structure. The system includes an aircraft comprising substantially composite material, and an impact-echo assembly for generating stress waves within and along a surface of the aircraft. The system also includes a data acquisition system capable of communicating with the impact-echo assembly such that the data acquisition system generates feedback indicative of at least a portion of the aircraft based on data from the impact-echo assembly.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
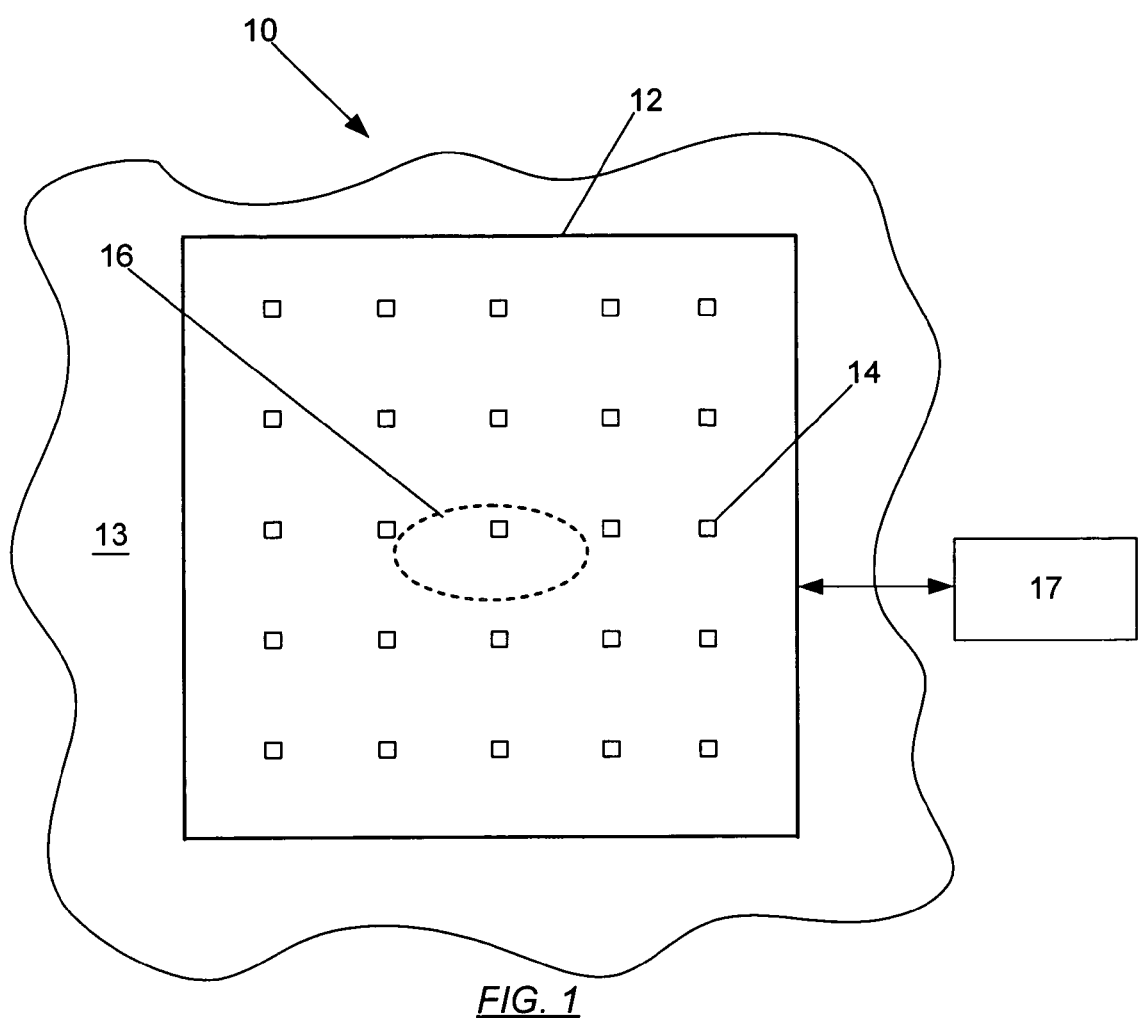
FIG. 1 is a plan view of an inspection system according to one embodiment of the present invention.

Referring now to the drawings and, in particular to FIG. 1, there is shown an inspection system 10. The inspection system 10 includes a flexible sheet of material 12 including a plurality of non-destructive sensors 14 arranged about the sheet. The sensors 14 are capable of detecting a flaw 16 in a structure material 13. As will be explained in greater detail below, an impact mechanism 24 is used to generate stress waves 22 along the surface and within the structure 13 such that the sensors 14 are capable of detecting the stress waves and determining whether a flaw is present. The sensors 14 are typically in communication with a data acquisition system 17 to generate various images of a portion of the structure based on data collected by the sensors.

The inspection system 10 could be used to inspect any number of structures 13 in a variety of industries where detection of flaws or defects in the structure is required, such as in the aircraft, automotive, or construction industries. The sensors are capable of detecting any number of flaws within or along the surface of the structure, such as cracks, disbonds, discontinuities, voids, or porosity, which could adversely affect the performance of the structure.

The term "structure" is not meant to be limiting, as the inspection system 10 could be used to inspect any number of parts or structures of different shapes and sizes, such as machined forgings, castings, or composite panels or parts. The inspection could be performed on newly manufactured structures or existing structures that are being inspected for preventative maintenance purposes. Further, the structure could be any number of materials. For example, the structure could be a metallic material, such as aluminum, or a composite material, such as graphite-epoxy. In addition, the structure material is generally a thin material that is used, for instance, as aircraft skin. For example, the structure could be an aircraft, such as the Boeing 787 or Boeing Dreamliner 7E7, where a substantial portion of the aircraft structure is a composite material (e.g., the fuselage and wings).

The flexible sheet of material 12 is typically a non-conductive sheet that is flexible and pliable. For example, the sheet of material 12 could be a thin polymeric material. Moreover, the flexible sheet of material 12 could also be a net-like sheet, where each of the sensors 14 are secured or otherwise connected, via strings, wires, or the like to the sheet of material. Thus, the flexible sheet of material 14 need not be a solid sheet of material, as the sheet could be an open net-like sheet including interconnected sensors 14 and locations for impacting the sheet. Providing a flexible sheet of material 12 allows the sheet to be manipulated to conform to a variety of surface contours for inspection, as well as maintain intimate contact with the underlying structure. The sheet of material 12 could be various dimensions to accommodate different sizes of structures for inspection. For example, the sheet of material 12 could be smaller than the structure under inspection and incrementally moved along the structure for inspecting portions of the structure.

Current paths to and from each sensor are incorporated (e.g., through some form of metallic deposition, etching, or bonding) or attached (e.g., via wires) to the flexible sheet of material 12. Each of the sensors 14 may be attached to this conductive network so that the sensors may communicate with the data acquisition system 17. The network serves to aggregate signals from sensors 14 such that a single cable connects the network to the data acquisition system 17 in a wireline embodiment. However, separate communication wires or cables may extend between each respective sensor 14 such that the network is not required. However, not including a conductive network and, instead, including several sensors 14 on a single sheet of material 12 may be undesirable as several wires or cables extending to the data acquisition system 17 may become difficult to manage or maneuver.

Figure 8:
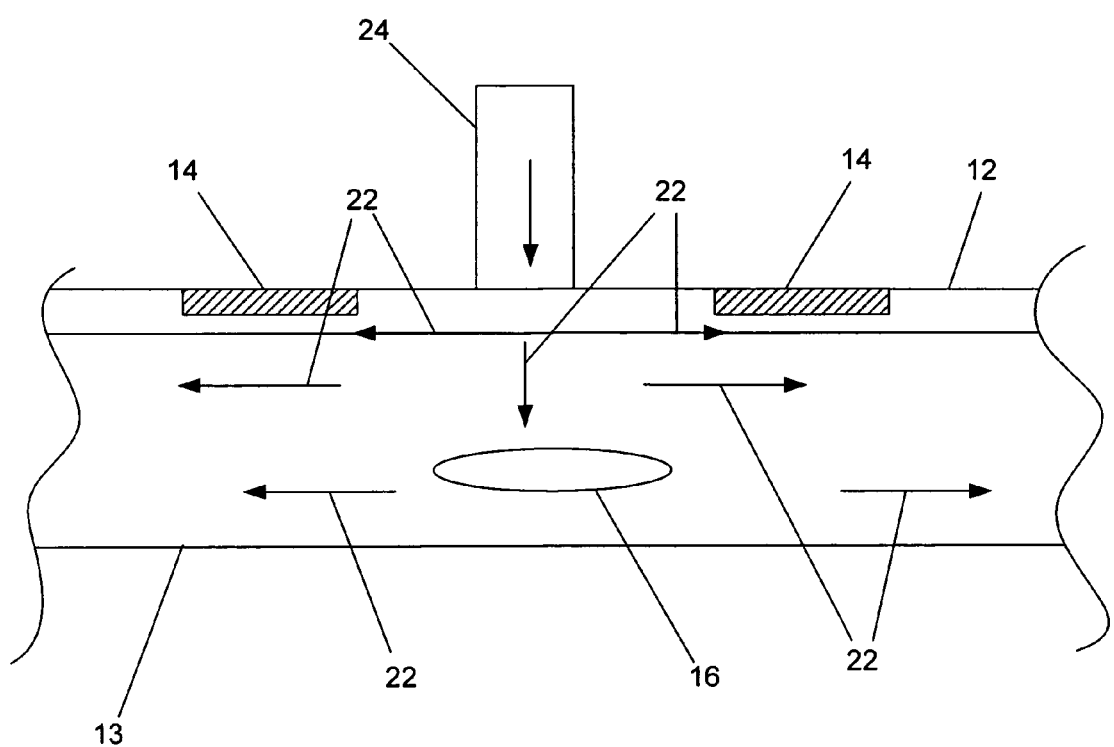
FIG. 8 is a cross-sectional view of an inspection system according to one embodiment of the present invention.

The flexible sheet of material 12 is placed adjacent to the structure 13 being inspected such that the sheet of material is touching or otherwise in contact with the structure, as shown in FIG. 8. Good contact between the sheet of material 12 and the structure is generally desired to ensure that the sensors 14 may detect stress waves 22 traveling through and along the structure. To ensure sufficient contact, a vacuum bag, vacuum frame, adhesive backing, an ultrasonic gel, or similar securing technique may be employed to temporarily secure the sheet of material 12 to the structure.

Each of the non-destructive sensors 14 could be any suitable sensor capable of generating information for inspecting a structure. Each sensor 14 is typically a non-destructive sensor, such that the sensor is capable of inspecting a structure without harming the structure or requiring disassembly of the structure. In the embodiment of the inspection system 10 shown in FIG. 1, each sensor 14 is an ultrasonic sensor, such as a piezo-electric sensor.

The sensors 14 are arranged on the flexible sheet of material 12 in a variety of configurations. For example, FIG. 1 illustrates that the sensors 14 are arranged linearly in rows in columns to define a 5×5 grid. Furthermore, in FIG. 6 the sensors 14 are located radially about the periphery of the sheet of material 12. However, it is understood that the sensors 14 may be arranged in any number of configurations on the sheet of material 12. As the number of sensors 14 increases, or the distance between the sensors decreases, the smaller the flaw that may be detected. Therefore, the number and/or arrangement of the sensors 14 may be varied depending on the size of the flaw to be detected and to achieve a particular resolution of the inspection image. The sensors 14 of the inspection system 10 may be reusable or disposable.

Figure 6:
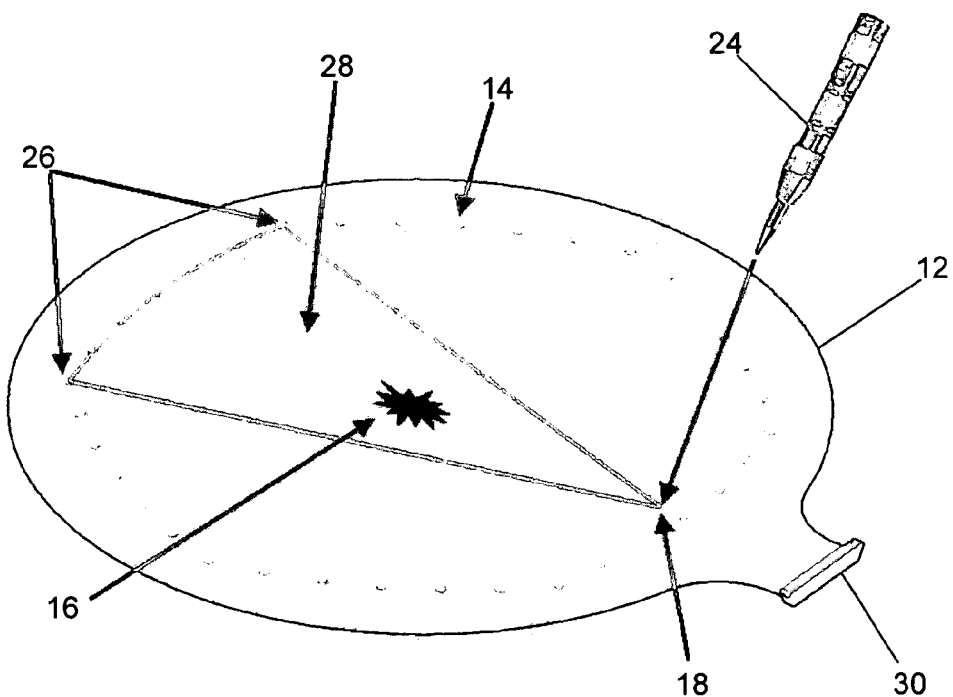
FIGS. 6-7 are perspective views of an additional inspection system according to one embodiment of the present invention.
Figure 7:
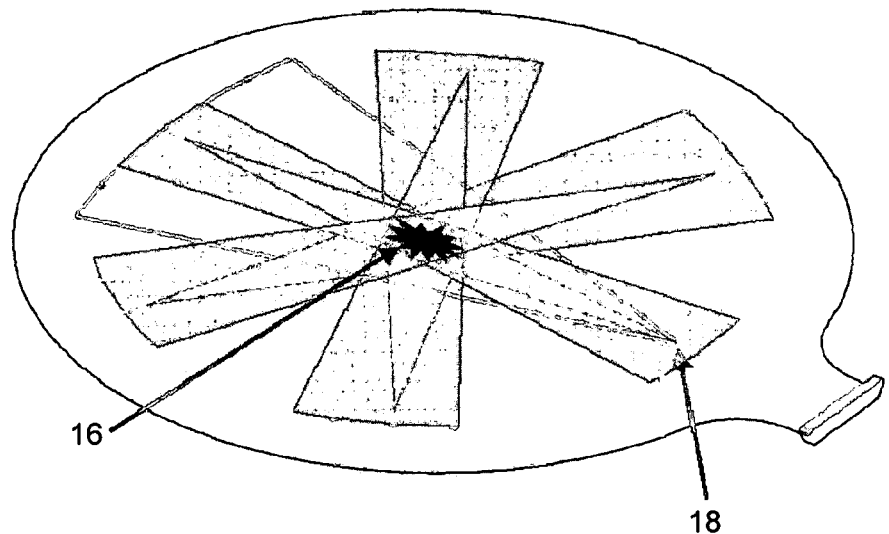

An impact mechanism 24 is used to generate stress waves 22 within and along the surface of the structure 13 to detect flaws 16, as shown in FIG. 8. For example, the mechanism could be a tapper, a tapper having a spring-loaded bar, one or more clickers, or a hammer. FIGS. 6 and 7 illustrate an impact mechanism 24, i.e., a clicker that could be a center punch, where pressing down on the housing of the clicker causes a mechanism to apply a force to the structure 13. Generally, the amount of force applied by the impact mechanism 24 is known so that a consistent force is applied to the structure 13. The impact mechanism 24 could be manually controlled by an inspector or automatically performed without human intervention. Moreover, a piezo-electric transducer activated by a high voltage pulse could be employed to generate stress waves. Thus, there could be various mechanisms used to generate stress waves 22 for a particular inspection system 10. FIG. 6 depicts a single impact mechanism 24, but the inspection system 10 could include one or more impact mechanisms, where multiple impact mechanisms could be activated simultaneously or sequentially. In addition, the impact mechanism 24 may be independent or separated from the sheet of material 12, or the impact mechanism could be integrated or built into the sheet of material.

A simple hand-held tap hammer could be used as an impact mechanism 24 if only time-of-flight information is used since the time of stress wave travel will not generally depend upon the level of impact. However, proper selection of impact duration and frequency content (by selecting a particular impact ball, for example) will determine how well the stress wave interacts with the interior damage structure. Frequency response, time-of-flight, or amplitude of the stress waves can be used, separately, or in combination to characterize and identify flaws within the structure 13. Thus, flaws may not only be identified and located, but the flaw could be characterized, such as by determining the depth of damage or the percent loss. Typically, the more information utilized, the better the characterization and identification of the flaws.

Figure 2:
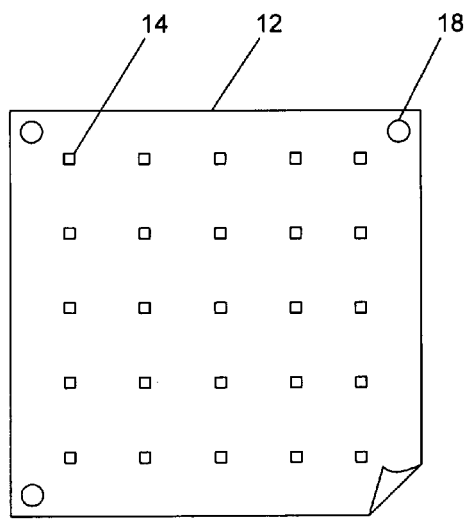
FIGS. 2-5 are plan views of inspection systems according to additional embodiments of the present invention.
Figure 3:
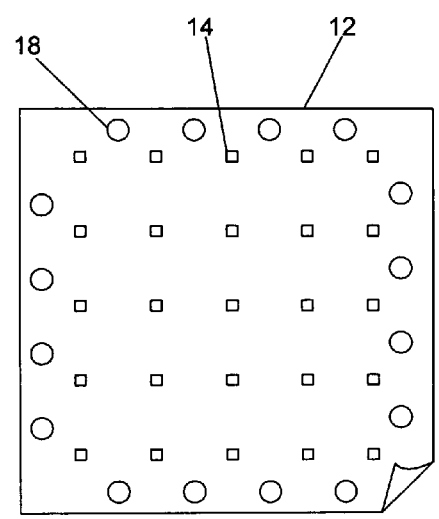
Figure 4:
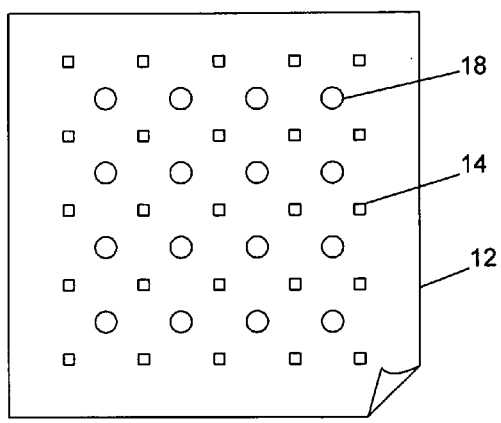
Figure 5:
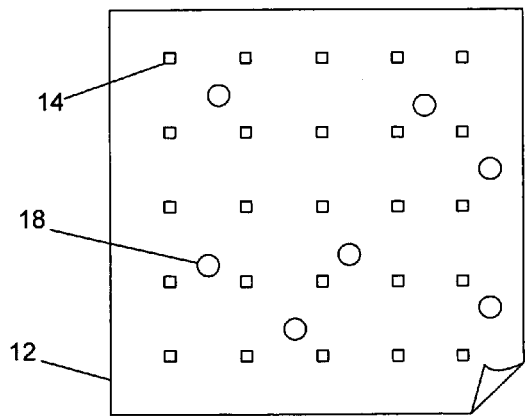

FIGS. 2-5 demonstrate that the location of applying the impact on the sheet of material 12 may vary. However, the location of impact is typically known so that a proper correlation may be made between the force applied and the distance between the impact and each of the sensors 14, which is explained in further detail below. FIG. 2 shows the impact locations 18 in each of the four corners of the flexible sheet of material 12, while FIG. 3 demonstrates that the impact may be made at several locations 18 around the edge of the sheet of material. FIG. 7 demonstrates a further example of applying the impact radially about the sheet of material 12, and in this particular embodiment, the impact is applied at six locations 18 about the periphery of the sheet of material. In addition, the impact locations 18 could be between rows of sensors 14, as shown in FIG. 4, or the impact locations could be at arbitrary locations, as shown in FIG. 5. Moreover, the impact locations could be proximate to the sheet of material 12 such that the impact mechanism could contact the edge of the sheet of material or contact the structure 13 slightly away from the sheet of material or between openings defined in a net-like sheet.

Impact locations 18 define where the stress waves 22 are initiated, and the number and location of which should be sufficient to produce enough impact-to-sensor paths to make a sufficient image for detecting potential flaws. The sheet of material 12 can have precisely located impact locations, as described above. However, precise locations may be unnecessary, since the location of impact can be determined through triangulation. If the speed or time of travel of a stress wave 22 through the structure 13 without flaws is known, the relative time it takes for the stress wave to reach individual sensors in the structure will define the impact location. This assumes that the edge of the sheet of material 12 where triangulation is being used is over flawless material since a near-by flaw will generally affect the triangulation results because it can change the speed of the stress wave 22. Selecting precise locations of impact typically simplifies the math and computer calculations required by the data acquisition system 17, while arbitrary impact locations typically require triangulation and more complicated reconstruction software. It is understood that one skilled in the art could readily design algorithms to analyze stress waves 22 and identify and/or characterize flaws in the structure 13 since these methods are generally known for this type of testing. The software may be made to be selectable, so that various impact options (e.g., impact location) are available.

In addition to the time of travel, the stress wave 22 amplitude data collected at each sensor 14 could provide valuable information. For example, a damaged area might not permit plate waves to pass through the structure 13 or may dramatically reduce its amplitude. If the locations of impact are precisely known, the amplitudes between impact can be normalized by comparing sensor data around the edge (where there is a flaw-free area) of equally spaced sensors 14. Those skilled in the art will recognize techniques to compare amplitudes to demonstrate that a flaw is located between the site of impact and the sensors 14. In general, either precise location or level of impact is desired. When both the location and level of impact is provided, the quality of the level of flaw detection is increased (since there is some redundancy), which typically provides simplification of the data analysis.

An inspector could observe the image formation in a batch process or in real time as he or she initiates impacts at various locations around the sheet of material 12. As the impact mechanism applies impact at more locations, the better the image will generally become, since the software would be designed to be able to add the results of new data into the forming image. The inspector could even initiate additional impact locations in one area or another to complete an image where data is missing.

When the impact mechanism generates one or more stress waves 22 on the surface of the structure 13 and within the structure on or near the flexible sheet of material 12, each sensor 14 will receive a signal at a particular time and of a particular amplitude. Depending on the type of material and thickness of the structure 13, the speed of the stress waves 22 may be determined when the impact mechanism applies a consistent force to the structure. Since the speed can be known or determined for a particular material and thickness, the path between impact and sensor 14 can be analyzed for damage. Thinning of the structure 13 due to disbonding, delamination, or corrosion thinning will affect the velocity of the plate wave. Furthermore, flaws or localized damage will obstruct the stress wave path. Since the sensor 14 locations are known, flaws or damage location and size can be mapped onto a grid that represents their locations on the structure 13.

FIGS. 6 and 7 illustrate another embodiment of the present invention where an impact mechanism 24 generates a stress wave at six distinct locations 18 about the periphery of the sheet of material 12. Each stress wave 22 propagates radially across the surface of the underlying structure 13 to define a circular sector between the location of impact 18 and a given number of sensors 26. Thus, multiple impact locations about the sheet of material 12 identify and bound the flaw 16. Time of flight between the impact locations 18 and respective sensors 26 along with characteristics of the stress wave may be used to quantify the flaw 16.

The data acquisition system 17 typically includes a processor or similar computing device operating under the control of imaging software so that any defects in the structure 13 may be presented on a display. It is possible to incorporate the data acquisition system 17 without a display and to instead provide a printout of the image scan, or to utilize any other technique for viewing the scan and location data. The processor could be embodied by a computer such as a desktop, laptop, or portable processing device capable of processing the data generated by the sensors 14 and creating an image, such as a B-scan or C-scan, of the scanned data that is shown on a display such as a monitor or other viewing device. The data acquisition system 17 is capable of generating images indicative of a flaw and may also allow a user to store and edit previously created images. Therefore, a permanent record of the images may be kept for future use or record keeping. However, it is understood that the data acquisition system 17 need not generate images, as the data acquisition system could mathematically collect and analyze data and generate, for example, time, amplitude, etc., that a technician could use to characterize a flaw based on the data.

Each sensor 14 is typically in communication with the data acquisition system 17, either directly or via the conductive network, to process the data accumulated by the sensors and to display the processed data. In many cases, communication cable(s) transmit data between the sheet of material 12, sensors 14, and the data acquisition system 17. For instance, FIGS. 6 and 7 depict a communication cable 30 that is capable of transmitting data acquired by the sensors 14 to the data acquisition system 17. The communication cable could be linked to a conductive network, as described above, to facilitate communication between several sensors 14 and the data acquisition system 17. In other embodiments, the data may be transmitted between the sensors 14 and the data acquisition system 17 via wireless communications, or at least between the conductive network and the data acquisition system. The sensors 14 may be directly connected to the processor, or indirectly connected, such as via a network. In further embodiments of the present invention the data acquisition system 17 may be located proximate to the sensors 14, such that remote connections between the sensor and data acquisition system are not necessary.

Thus, the present invention provides several advantages. The inspection system 10 provides image-based ultrasonic array data at a lower cost than conventional pulse-echo testing techniques by eliminating the need for a high voltage pulser, a more costly pulser/receiver card, and more costly transducer materials. Due to the relative simplicity and reduced cost of the inspection system, the sensors 14 may be reusable or even disposable.

Furthermore, the inspection system 10 collects data more rapidly than most conventional scanning systems. Although the inspection system 10 may provide a less complete data set in certain circumstances when compared to conventional scanning systems, the resolution of the inspection system 10 is sufficient for many in-service aerospace applications, such as impact damage inspection. The inspection system 10 also provides quantitative image-based data that conventional hand-held ultrasonic testing and tap testing cannot provide.

The inspection system 10 enables rapid inspection of composite and metallic structures. For composite structures, the inspection system 10 can quantify impact damage area size and shape and verify that there are no large voids in composite-composite or composite-metal repairs. For metallic structures, the inspection system 10 can be used to quantify material thinning due to corrosion or locate cracks as a result of fatigue or damage.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for identifying defects in a structure comprising:
    a flexible sheet of material positioned adjacent to the structure;
    a plurality of non-destructive sensors secured to the flexible sheet;
    a mechanism operable to externally apply a plurality of impacts onto the flexible sheet and/or onto the structure proximate to the flexible sheet at a plurality of locations to generate stress waves within and along a surface of the structure, wherein the mechanism is operable to externally apply each impact onto the flexible sheet at a different predetermined location and with a predetermined magnitude; and
    a data acquisition system capable of communicating with the sensors such that the data acquisition system generates feedback indicative of at least a portion of the structure based on accumulated data from the stress waves acquired by the sensors and further based on the predetermined location and the predetermined magnitude at which each of the plurality of impacts is applied.

2. The system according to claim 1, wherein the flexible sheet of material comprises a non-conductive material.

3. The system according to claim 1, wherein the flexible sheet of material is capable of being secured to the structure using one of a vacuum bag, vacuum frame,
    an adhesive backing, and an ultrasonic gel.

4. The system according to claim 1, wherein the sensors comprise piezo-electric sensors.

5. The system according to claim 1, wherein the sensors are arranged about the periphery of the flexible sheet of material.

6. The system according to claim 1, wherein the sensors are arranged in a grid on the flexible sheet of material.

7. The system according to claim 1, wherein the data acquisition system comprises a processor for creating an image including information for detecting a defect in the structure.

8. The system according to claim 1, wherein the mechanism comprises one of a tapper, a tapper having a spring-loaded bar, one or more clickers, and a hammer.

9. The system according to claim 1, wherein the structure comprises one of a metallic and composite material.

10. An assembly for identifying defects comprising:
    a structure comprising one of a metallic and composite material;
    a flexible sheet of material positioned adjacent to the structure;
    a plurality of non-destructive sensors secured to the flexible sheet; and
    a mechanism operable to externally apply a plurality of impacts onto the flexible sheet and/or onto the structure proximate to the flexible sheet to generate stress waves within and along a surface of the structure, wherein the mechanism is operable to apply each of the plurality of impacts at a different predetermined location and with a predetermined magnitude.

11. The assembly according to claim 10, wherein the flexible sheet of material comprises a non-conductive material.

12. The assembly according to claim 11, wherein the flexible sheet of material comprises a polymeric material.

13. The assembly according to claim 10, wherein the flexible sheet of material is capable of being secured to the structure using one of a vacuum bag, vacuum frame, an adhesive backing, and an ultrasonic gel.

14. The assembly according to claim 10, wherein the sensors comprise piezo-electric sensors.

15. The assembly according to claim 10, wherein the sensors are arranged about the periphery of the flexible sheet of material.

16. The assembly according to claim 10, wherein the sensors are arranged in a grid about the flexible sheet of material.

17. The assembly according to claim 10, wherein the mechanism comprises one of a tapper, a tapper having a spring-loaded bar, one or more clickers, and a hammer.

18. A method for identifying defects in a structure utilizing a plurality of non-destructive sensors secured to a flexible sheet of material, the method comprising:
  positioning the flexible sheet of material adjacent to the structure;
  applying a plurality of external impacts onto the flexible sheet and/or onto the structure proximate to the flexible sheet, wherein each of the plurality of impacts is applied at a different predetermined location and with a predetermined magnitude to generate stress waves within and along a surface of the structure; and
  detecting the stress waves with the sensors and deriving data from the stress waves that is indicative of at least a portion of the structure and that is based on accumulated data derived from the stress waves and the predetermined location and the predetermined magnitude at which each of the plurality of impacts is applied.

19. The method according to claim 18, further comprising securing the flexible sheet of material to the structure using one of a vacuum bag, vacuum frame, an adhesive backing, and an ultrasonic gel.

20. The method according to claim 18, wherein applying comprises impacting the flexible sheet of material with one of a tapper, a tapper having a spring-loaded bar, one or more clickers, and a hammer.

21. The method according to claim 18, wherein applying comprises impacting the flexible sheet of material and structure one of manually and automatically.

22. The method according to claim 18, wherein applying comprises impacting about the periphery of the flexible sheet of material.

23. The method according to claim 18, wherein applying comprises impacting the flexible sheet of material in a predetermined pattern.

24. The method according to claim 18, further comprising communicating the data acquired by the sensors to a data acquisition system and creating an image of at least a portion of the structure with the data acquisition system based on the data acquired by the sensors.

25. A system for identifying defects in an aircraft structure comprising:
  an aircraft comprising substantially composite material;
  an impact-echo assembly for externally applying a plurality of impacts onto the aircraft, wherein each of the plurality of impacts is applied with a predetermined magnitude and at a different predetermined location to generate stress waves within and along a surface of the aircraft; and
  a data acquisition system capable of communicating with the impact-echo assembly such that the data acquisition system generates feedback indicative of at least a portion of the aircraft based on accumulated data from the impact-echo assembly and further based on the predetermined location and magnitude at which each force of the plurality of impacts is applied.

26. The system according to claim 25, wherein the impact-echo assembly comprises:
  a flexible sheet of material positioned adjacent to the aircraft;
  a plurality of non-destructive sensors secured to the flexible sheet; and
  a mechanism operable to impact the flexible sheet or proximate to the flexible sheet to generate the stress waves.

27. The system according to claim 25, wherein the data acquisition system creates an image comprising information for detecting a defect in the aircraft.

* * * * *